US010500195B2

(12) United States Patent
Patil et al.

(10) Patent No.: US 10,500,195 B2
(45) Date of Patent: Dec. 10, 2019

(54) ANTIBACTERIAL COMPOUNDS

(71) Applicant: WOCKHARDT LIMITED, Chikalthana, Aurangabad (IN)

(72) Inventors: Vijaykumar Jagdishwar Patil, Solapur (IN); Ravikumar Tadiparthi, Aurangabad (IN); Piyush Ambalal Patel, Gujarat (IN); Rajib Bhuniya, West Bengal (IN); Sachin Bhagwat, Aurangabad (IN); Swapna Shripad Takalkar, Aurangabad (IN); Rajesh Chavan, Aurangabad (IN); Anusuya Patel, Auranagabad (IN); Vipul Rane, Auranagabad (IN); Mahesh Vithalbhai Patel, Aurangabad (IN)

(73) Assignee: WOCKHARDT LIMITED, Chikalthana, Aurangabad (IN)

( * ) Notice: Subject to any disclaimer, the term of this patent is extended or adjusted under 35 U.S.C. 154(b) by 0 days.

(21) Appl. No.: 15/547,487

(22) PCT Filed: Apr. 24, 2017

(86) PCT No.: PCT/IB2017/052330
§ 371 (c)(1),
(2) Date: Jul. 29, 2017

(87) PCT Pub. No.: WO2018/158619
PCT Pub. Date: Sep. 7, 2018

(65) Prior Publication Data

US 2018/0250276 A1 Sep. 6, 2018

(30) Foreign Application Priority Data

Mar. 2, 2017 (IN) ............................. 201721007393

(51) Int. Cl.

| | |
|---|---|
| ***A61K 31/439*** | (2006.01) |
| ***A61P 31/04*** | (2006.01) |
| *A61K 45/06* | (2006.01) |
| *A61K 31/34* | (2006.01) |
| *A61K 31/397* | (2006.01) |
| *A61K 31/382* | (2006.01) |
| *A61K 31/4188* | (2006.01) |

(52) U.S. Cl.
CPC ............ *A61K 31/439* (2013.01); *A61P 31/04* (2018.01); *A61K 31/34* (2013.01); *A61K 31/382* (2013.01); *A61K 31/397* (2013.01); *A61K 31/4188* (2013.01); *A61K 45/06* (2013.01); *A61K 2300/00* (2013.01)

(58) Field of Classification Search
CPC .................................................... A61K 31/439
See application file for complete search history.

(56) References Cited

U.S. PATENT DOCUMENTS 8,822,450 B2 * 9/2014 Patel .................. A61K 31/4545
514/210.2
9,732,081 B2 * 8/2017 Patil ..................... A61K 31/439

FOREIGN PATENT DOCUMENTS

WO WO-2014033560 A1 * 3/2014 ........... A61K 31/439

OTHER PUBLICATIONS

Wakefield, Basil "Fluorinated Pharmaceuticals" Innovations in Pharmaceutical Technology 2003, 74, 76-78.*
Jim O'Neil's publication, 2016. UK government report on antimicrobial resistance (AMR).
Nature Biotechnology vol. 36 No. 7 Jul. 2018, p. 555.

* cited by examiner

*Primary Examiner* — David K O'Dell
(74) *Attorney, Agent, or Firm* — Bio Intellectual Property Services LLC (Bio IPS); O. (Sam) Zaghmout

(57) ABSTRACT

Compounds of Formula (I), or a stereoisomer or a pharmaceutically acceptable salt thereof, their preparation, pharmaceutical compositions comprising such compounds and their use in treating and/or preventing bacterial infections are disclosed.

Formula (I)

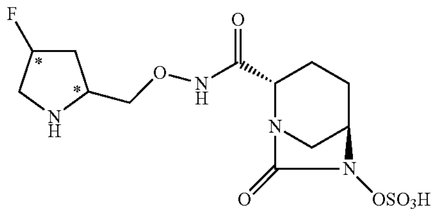

26 Claims, No Drawings

ANTIBACTERIAL COMPOUNDS

RELATED PATENT APPLICATIONS

This application claims the priority to and benefit of Indian Provisional Patent Application No. 201721007393 filed on Mar. 2, 2017; the disclosures of which are incorporated herein by reference in its entirety as if fully rewritten herein.

FIELD OF THE INVENTION

The invention relates to fluorine containing compounds, their preparation and their use in treating and/or preventing bacterial infections.

BACKGROUND OF THE INVENTION

The emergence of bacterial resistance to known antibacterial agents is becoming a major challenge in treating bacterial infections. One way forward to treat bacterial infections, and especially those caused by resistant bacteria, is to develop new antibacterial agents that can overcome the bacterial resistance. Coates et al. (Br. J. Pharmacol. 2007; 152(8), 1147-1154) have reviewed approaches to developing new antibiotics. However, the development of new antibacterial agents is a challenging task. For example, Gwynn et al. (Annals of the New York Academy of Sciences, 2010, 1213: 5-19) have reviewed the challenges in the discovery of antibacterial agents. Several antibacterial agents have been described in the prior art. However, there remains a need for potent antibacterial agents for use in treatment and/or prevention of bacterial infections, including those caused by bacteria that have acquired resistance to one or more of the known antibacterial agents. The inventors have surprisingly discovered certain fluorine containing compounds having antibacterial properties.

SUMMARY OF THE INVENTION

Accordingly, there are provided fluorine containing compounds, methods for preparation of these compounds, pharmaceutical compositions comprising these compounds, and methods for treating and/or preventing bacterial infection in a subject using these compounds.

In one general aspect, there is provided a compound of Formula (I),

Formula (I)

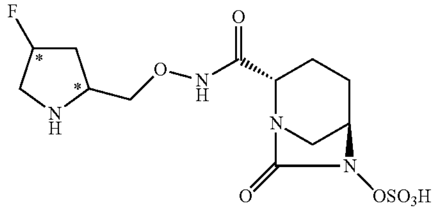

or a stereoisomer or a pharmaceutically acceptable salt thereof.

In another general aspect, there are provided pharmaceutical compositions comprising a compound of Formula (I), or a stereoisomer or a pharmaceutically acceptable salt thereof.

In another general aspect, there is provided a method for treating or preventing a bacterial infection in a subject, said method comprising administering to said subject a compound of Formula (I) or a stereoisomer or a pharmaceutically acceptable salt thereof.

In yet another general aspect, there is provided a method for treating or preventing a bacterial infection in a subject, said method comprising administering to said subject a pharmaceutical composition comprising a compound of Formula (I) or a stereoisomer or a pharmaceutically acceptable salt thereof.

In another general aspect, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for treating or preventing a bacterial infection in a subject, said method comprising administering to said subject a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In another general aspect, there is provided a method for treating or preventing a bacterial infection in a subject, said method comprising administering to said subject: (a) a compound of Formula (I), or a stereoisomer or a pharmaceutically acceptable salt thereof, and (b) at least one antibacterial agent or a pharmaceutically acceptable derivative thereof.

In another general aspect, there are provided methods for increasing antibacterial effectiveness of a antibacterial agent in a subject, said method comprising co-administering said antibacterial agent or a pharmaceutically acceptable derivative thereof with a compound of Formula (I) or a stereoisomer or a pharmaceutically acceptable salt thereof.

In another general aspect, there is provided a process for preparing a compound of Formula (I) or a stereoisomer or a pharmaceutically acceptable salt thereof.

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one of ordinary skills in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety.

The inventors have surprisingly discovered certain fluorine containing compounds having antibacterial properties.

The term "stereoisomers" as used herein refers to and includes compounds that have identical chemical constitution, but differ with regard to the arrangement of their atoms or groups in space. The compounds of Formula (I) contains asymmetric or chiral centres (including those marked with "*") and, therefore, exist in different stereoisomeric forms. It is intended, unless specified otherwise, that all stereoisomeric forms of the compounds of Formula (I) as well as mixtures thereof, including racemic mixtures, form part of the present invention. In addition, all geometric and positional isomers (including cis and trans-forms) as well as mixtures thereof, are also embraced within the scope of the invention. In general, a reference to a compound is intended to cover its stereoisomers and a mixture of various stereoisomers.

The term "pharmaceutically acceptable salt" as used herein refers to one or more salts of a given compound which possesses the desired pharmacological activity of the free compound and which are neither biologically nor otherwise undesirable. In general, the "pharmaceutically acceptable salts" refer to and include those salts that are suitable for use in contact with the tissues of human and animals without undue toxicity, irritation, allergic response and the like, and are commensurate with a reasonable benefit/risk ratio. Pharmaceutically acceptable salts are well known in the art. For example, S. M. Berge, et al. (J. Pharmaceutical Sciences, 66: 1-19 (1977)), incorporated herein by reference in its entirety, describes various pharmaceutically acceptable salts in details.

In general, the compounds according to the invention contain basic (e.g. nitrogen atoms) as well as acid moieties (e.g. $SO_3H$ group). A person of skills in the art would appreciate that such compounds, therefore, can form acidic salts (formed with inorganic and/or organic acids), as well as basic salts (formed with inorganic and/or organic bases). Such salts can be prepared using procedures described in the art. For example, the basic moiety can be converted to its salt by treating a compound with a suitable amount of acid. Typical, non-limiting examples of such suitable acids include hydrochloric acid, trifluoroacetic acid, methanesulphonic acid, or the like. Alternatively, the acid moiety may be converted into its salt by treating with a suitable base. Typical non-limiting examples of such bases include sodium carbonate, sodium bicarbonate, potassium carbonate, potassium bicarbonate or the like. In case of compounds containing more than one functional group capable of being converted into salt, each such functional group may be converted to a salt independently. For example, in case of compounds containing two basic nitrogen atoms, one of the basic nitrogen can form salt with one acid while the other basic nitrogen can form salt with another acid. The compounds according to the invention contain both, acidic as well as basic moieties, and thus can form inner salts or corresponding zwitterions. In general, all pharmaceutically acceptable salt forms of compounds of Formula (I) according to invention including acid addition salts, base addition salts, zwitterions or the like are contemplated to be within the scope of the present invention and are generically referred to as pharmaceutically acceptable salts.

The term "infection" or "bacterial infection" as used herein refers to and includes presence of bacteria, in or on a subject, which, if its growth were inhibited, would result in a benefit to the subject. As such, the term "infection" in addition to referring to the presence of bacteria also refers to normal flora, which is not desirable. The term "infection" includes infection caused by bacteria.

The term "treat", "treating" or "treatment" as used herein refers to administering a medicament, including a pharmaceutical composition, or one or more pharmaceutically active ingredients, for prophylactic and/or therapeutic purposes. The term "prophylactic treatment" refers to treating a subject who is not yet infected, but who is susceptible to, or otherwise at a risk of infection (preventing the bacterial infection). The term "therapeutic treatment" refers to administering treatment to a subject already suffering from infection. The terms "treat", "treating" or "treatment" as used herein also refer to administering compositions or one or more of pharmaceutically active ingredients discussed herein, with or without additional pharmaceutically active or inert ingredients, in order to: (i) reduce or eliminate either a bacterial infection or one or more symptoms of the bacterial infection, or (ii) retard the progression of a bacterial infection or of one or more symptoms of the bacterial infection, or (iii) reduce the severity of a bacterial infection or of one or more symptoms of the bacterial infection, or (iv) suppress the clinical manifestation of a bacterial infection, or (v) suppress the manifestation of adverse symptoms of the bacterial infection.

The term "pharmaceutically effective amount" or "therapeutically effective amount" or "effective amount" as used herein refers to an amount, which has a therapeutic effect or is the amount required to produce a therapeutic effect in a subject. For example, a therapeutically or pharmaceutically effective amount of an antibacterial agent or a pharmaceutical composition is the amount of the antibacterial agent or the pharmaceutical composition required to produce a desired therapeutic effect as may be judged by clinical trial results, model animal infection studies, and/or in vitro studies (e.g. in agar or broth media). The pharmaceutically effective amount depends on several factors, including but not limited to, the microorganism (e.g. bacteria) involved, characteristics of the subject (for example height, weight, sex, age and medical history), severity of infection and the particular type of the antibacterial agent used. For prophylactic treatments, a therapeutically or prophylactically effective amount is that amount which would be effective in preventing a microbial (e.g. bacterial) infection. The compounds and/or pharmaceutical compositions according to the invention are used in amounts that are effective in providing the desired therapeutic effect or result.

The term "administration" or "administering" includes delivery of a composition or one or more pharmaceutically active ingredients to a subject, including for example, by any appropriate methods, which serves to deliver the composition or its active ingredients or other pharmaceutically active ingredients to the site of the infection. The method of administration may vary depending on various factors, such as for example, the components of the pharmaceutical composition or the nature of the pharmaceutically active or inert ingredients, the site of the potential or actual infection, the microorganism involved, severity of the infection, age and physical condition of the subject and a like. Some non-limiting examples of ways to administer a composition or a pharmaceutically active ingredient to a subject according to this invention includes oral, intravenous, topical, intra-respiratory, intra-peritoneal, intra-muscular, parenteral, sublingual, transdermal, intranasal, aerosol, intra-ocular, intra-tracheal, intra-rectal, vaginal, gene gun, dermal patch, eye drop, ear drop or mouthwash. In case of a pharmaceutical composition comprising more than one ingredient (active or inert), one of way of administering such composition is by admixing the ingredients (e.g. in the form of a suitable unit dosage form such as tablet, capsule, solution, powder and a like) and then administering the dosage form. Alternatively, the ingredients may also be administered separately (simultaneously or one after the other) as long as these ingredients reach beneficial therapeutic levels such that the composition as a whole provides a synergistic and/or the desired effect.

The term "growth" as used herein refers to a growth of one or more microorganisms and includes reproduction or population expansion of the microorganism (e.g. bacteria). The term "growth" also includes maintenance of on-going metabolic processes of a microorganism (e.g. bacteria), including processes that keep the microorganism alive.

The term, "effectiveness" as used herein refers to ability of a treatment or a composition or one or more pharmaceutically active ingredients to produce a desired biological effect in a subject. For example, the term "antibacterial effectiveness" of a composition or an antibacterial agent refers to the ability of the composition or the antibacterial agent to treat or prevent the microbial (e.g. bacterial) infection in a subject.

The term "synergistic" or "synergy" as used herein refers to the interaction of two or more agents so that their combined effect is greater than their individual effects.

The term "antibacterial agent" as used herein refers to any substance, compound or a combination of substances or a combination compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

The term "beta-lactam antibacterial agent" as used herein refers to compounds with antibacterial properties and containing a beta-lactam nucleus in their molecular structure.

The term "beta-lactamase" as used herein refers to any enzyme or protein or any other substance that breaks down a beta-lactam ring. The term "beta-lactamase" includes enzymes that are produced by bacteria and have the ability to hydrolyse the beta-lactam ring in a beta-lactam compound, either partially or completely.

The term "beta-lactamase inhibitor" as used herein refers to a compound capable of inhibiting activity of one or more beta-lactamase enzymes, either partially or completely.

The term "pharmaceutically inert ingredient" or "carrier" or "excipient" refers to a compound or material used to facilitate administration of a compound, including for example, to increase the solubility of the compound. Typical, non-limiting examples of solid carriers include, starch, lactose, dicalcium phosphate, sucrose, and kaolin and so on. Typical, non-limiting examples of liquid carriers include sterile water, saline, buffers, non-ionic surfactants, and edible oils such as oil, peanut and sesame oils and so on. In addition, various adjuvants commonly used in the art may be included. These and other such compounds are described in the literature, for example, in the Merck Index (Merck & Company, Rahway, N.J.). Considerations for inclusion of various components in pharmaceutical compositions are described, for example, in Gilman et al. (Eds.) (1990); Goodman and Gilman's: The Pharmacological Basis of Therapeutics, 8th Ed., Pergamon Press., which is incorporated herein by reference in its entirety.

The term "subject" as used herein refers to a vertebrate or invertebrate, including a mammal. The term "subject" includes human, animal, a bird, a fish, or an amphibian. Typical, non-limiting examples of a "subject" includes humans, cats, dogs, horses, sheep, bovine cows, pigs, lambs, rats, mice and guinea pigs.

The term "pharmaceutically acceptable derivative" as used herein refers to and includes any pharmaceutically acceptable salt, pro-drugs, metabolites, esters, ethers, hydrates, polymorphs, solvates, complexes, enantiomers or adducts of a compound described herein which, upon administration to a subject, is capable of providing (directly or indirectly) the parent compound. For example, the term "antibacterial agent or a pharmaceutically acceptable derivative thereof" includes all derivatives of the antibacterial agent (such as salt, pro-drugs, metabolites, esters, ethers, hydrates, polymorphs, solvates, complexes, enantiomers or adducts) which, upon administration to a subject, is capable of providing (directly or indirectly) the antibacterial compound.

In one general aspect, there is provided a compound of Formula (I),

Formula (I)

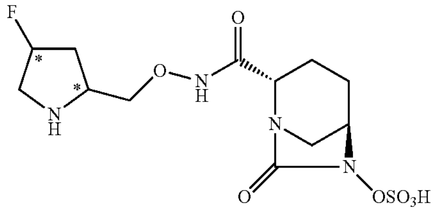

or a stereoisomer or a pharmaceutically acceptable salt thereof.

Typical, non-limiting examples of compounds according to the invention include:

(2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

Sodium salt of (2S, 5R-N-{[(2S, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide; and Potassium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide.

The compounds of the invention can be prepared according to the general procedure given in Scheme 1. Individual stereoisomers can be prepared using appropriate starting materials and reagents. A person of skills in the art would appreciate that the described methods can be varied and/or optimized further to provide the desired and related compounds.

Formula (V) is converted into a compound of Formula (VI) in presence of suitable reagents. The compound of Formula (VI) is then reacted with a sodium salt of (2S, 5R)-6-benzyloxy-7-oxo-1,6-diaza-bicyclo [3.2.1] octane-2-carboxylic acid (VII) to obtain a compound of Formula (VIII). The compound of Formula (VIII) is then converted into a compound of Formula (IX) in presence of a suitable debenzylating agent. Typical, not-limiting examples of suitable debenzylating agents include hydrogen gas in presence of a transition metal catalyst such as palladium on carbon. The compound of Formula (IX) is converted into a compound of Formula (X) in presence of a suitable sulfonating agent. Typical, not-limiting examples of suitable sulfonating agents include sulfur trioxide dimethylformamide complex. The sulfonation reaction is followed by treatment with tetrabutylammonium acetate to obtain a compound of Formula (X). The compound of Formula (X) is converted into a com- Scheme 1

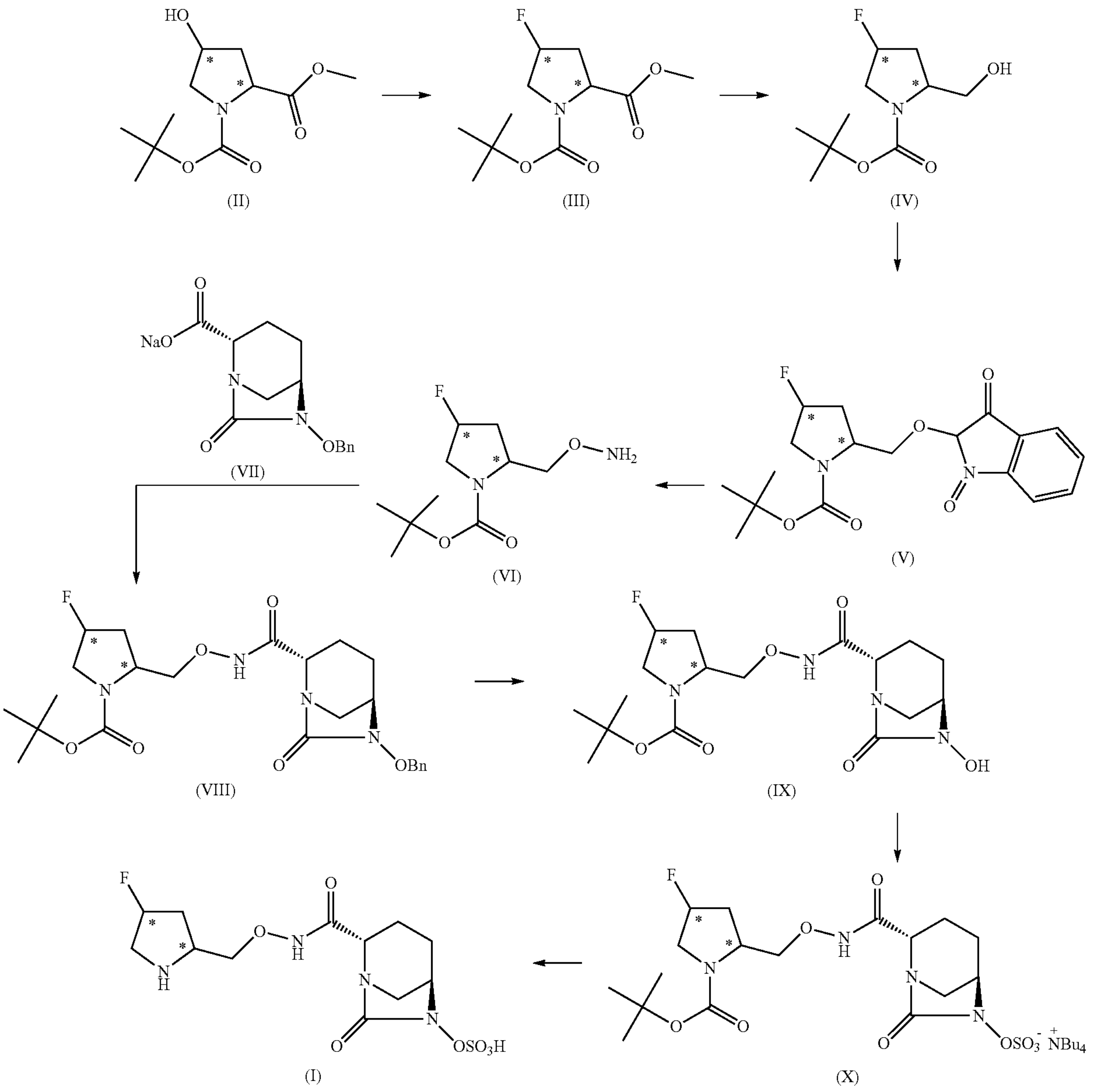

Typically, a compound of Formula (II) is converted into a compound of Formula (III) in the presence of a suitable fluorinating agent. Typical, non-limiting examples of suitable fluorinating agents include diethylaminosulfur trifluoride (DAST reagent). The compound of Formula (III) is then converted into a compound of Formula (IV) in presence of a suitable reducing agent. Typical, non-limiting examples of suitable reducing agents include lithium borohydride. The compound of Formula (IV) is converted into a compound of Formula (V) using suitable reagents. The compound of pound of Formula (I) in presence of a suitable de-protecting agent. Typical, not-limiting examples of suitable de-protecting agents include trifluoroacetic acid. A wide variety of other reagents which can bring about these functional transformations can also be used.

In some embodiments, there are provided pharmaceutical compositions comprising a compound of Formula (I), or a stereoisomer or a pharmaceutically acceptable salt thereof.

In some embodiments, there are provided pharmaceutical compositions comprising a compound which is (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

In some embodiments, there are provided pharmaceutical compositions comprising: (a) a compound of Formula (I), or a stereoisomer or a pharmaceutically acceptable salt thereof, and (b) at least one antibacterial agent or a pharmaceutically acceptable derivative thereof.

In some embodiments, there are provided pharmaceutical compositions comprising: (a) (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof, and (b) at least one antibacterial agent or a pharmaceutically acceptable derivative thereof.

In some embodiments, there are provided pharmaceutical compositions comprising: (a) (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof, and (b) one or more of cefixime, cefpodoxime, ceftibuten, cefuroxime, or a pharmaceutically acceptable salt thereof.

In some other embodiments, there are provided methods for treating or preventing a bacterial infection in a subject, said method comprising administering to said subject, compounds or pharmaceutical compositions according to the invention.

In some other embodiments, there are provided methods for treating or preventing bacterial infection in a subject, said method comprising administering to said subject a compound of Formula (I), or a stereoisomer or a pharmaceutically acceptable salt thereof.

In some embodiments, there are provided methods for treating or preventing bacterial infection in a subject, said method comprising administering to said subject a pharmaceutical composition comprising a compound of Formula (I) or a stereoisomer or a pharmaceutically acceptable salt thereof.

In other embodiments, there are provided methods for treating or preventing a bacterial infection in a subject, said method comprising administering to said subject a pharmaceutical composition comprising: (a) a compound of Formula (I), or a stereoisomer or a pharmaceutically acceptable salt thereof, and (b) at least one antibacterial agent or a pharmaceutically acceptable derivative thereof.

In few other embodiments, there are provided methods for treating or preventing a bacterial infection in a subject, said method comprising administering to said subject: (a) a compound of Formula (I), or a stereoisomer or a pharmaceutically acceptable salt thereof, and (b) at least one antibacterial agent or a pharmaceutically acceptable derivative thereof.

In some embodiments, there are provided methods for increasing antibacterial effectiveness of a antibacterial agent in a subject, said method comprising co-administering said antibacterial agent or a pharmaceutically acceptable derivative thereof with a compound of Formula (I), or a stereoisomer or a pharmaceutically acceptable salt thereof.

In some embodiments, the compounds and/or the compositions according to the invention are used in treating or preventing bacterial infection.

In some embodiments, there is provided for use of a compound which is (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof, in treating or preventing a bacterial infection.

In some embodiments, a compound which is (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof, is used in the preparation of a medicament for treating or preventing a bacterial infection.

In some embodiments, there is provided a method for treating or preventing bacterial infection in a subject, said method comprising administering to said subject a compound which is (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof.

In some embodiments, there is provided a method for treating or preventing bacterial infection in a subject, said method comprising administering to said subject a pharmaceutical composition comprising (2S, 5R)-N-{[(2S, 4S)-4-fluoropyrrolidin-2-yl]methyloxy}-7-oxo-6-(sulfooxy)-1,6-diazabicyclo [3.2.1] octane-2-carboxamide, or a stereoisomer or a pharmaceutically acceptable salt thereof.

In some embodiments, there is provided a method for treating or preventing bacterial infection in a subject, said method comprising administering to said subject, a pharmaceutical composition comprising: (a) (2S, 5R)-N-{[(2S, 4S)-4-fluoropyrrolidin-2-yl]methyloxy}-7-oxo-6-(sulfooxy)-1,6-diazabicyclo [3.2.1]octane-2-carboxamide, or a stereoisomer or a pharmaceutically acceptable salt thereof, and (b) at least one antibacterial agent or a pharmaceutically acceptable derivative thereof.

In some embodiments, there is provided a method for treating or preventing bacterial infection in a subject, said method comprising administering to said subject a pharmaceutical composition comprising: (a) (2S, 5R)-N-{[(2S, 4S)-4-fluoropyrrolidin-2-yl]methyloxy}-7-oxo-6-(sulfooxy)-1,6-diazabicyclo [3.2.1]octane-2-carboxamide, or a stereoisomer or a pharmaceutically acceptable salt thereof, and (b) one or more of cefixime, cefpodoxime, ceftibuten, cefuroxime, or a pharmaceutically acceptable salt thereof.

The compositions and methods according to the invention use compounds of Formula (I) or a stereoisomer or a pharmaceutically acceptable salt thereof, in combination with at least one antibacterial agent or a pharmaceutically acceptable derivative thereof. A wide variety of antibacterial agents can be used in combination with the compounds according to the invention. The antibacterial agents are often classified depending on their structure or mode of action.

Typical, non-limiting examples of antibacterial agents include those belonging to a group of antibacterial agents such as Ansamycins, Carbacephems, Carbapenams, Carbapenems, Cephalosporins, Cephamycins, Cephems, Lincosamides, Lipopeptides, Macrolides, Ketolides, Monobactams, Nitrofurans, Oxacephems, Oxapenams, Oxazolidinones, Penams, Penems, Penicillins, Polypeptides, Quinolones, Sulfonamides, Tetracyclines, and a like.

In some embodiments, the antibacterial agent is a beta-lactam antibacterial agent.

Typical, non-limiting, examples of a beta-lactam antibacterial agents include those generally known as Carbacephems, Carbapenams, Carbapenems, Cephalosporins, Cephamycins, Cephems, Monobactams, Oxacephems, Oxapenams, Penams, Penems, Penicillins and a like.

Typical, non-limiting, examples of antibacterial agents include cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefclidin, cefdaloxime, cefdinir, cefditoren, cefepime, cefetamet, cefixime, cefluprenam, cefmenoxime, cefmetazole, cefminox, cefodizime, cefonicid, cefoperazone, ceforanide, cefoselis, cefotaxime, cefotetan, cefotiam, cefovecin, cefoxitin, cefoxitin, cefozopran, cefpimizole, cefpiramide, cefpirome, cefpodoxime, cefprozil, cefquinome, cefradine, cefroxadine, cefsulodin, ceftaroline, ceftazidime, cefteram, ceftezole, ceftibuten, ceftiofur, ceftiolene, ceftizoxime, ceftobiprole, ceftolozane, ceftriaxone, cefuroxime, cefuzonam, cephaloridine, cephradine, CXA-101, flomoxef, latamoxef, loracarbef, moxalactam and a like.

In some embodiments, the antibacterial agent is at least one selected from cefaclor, cefadroxil, cefalexin, cefdinir, cefixime, cefpodoxime, cefprozil, cefradine, ceftibuten, cefuroxime, loracarbef or a pharmaceutically acceptable derivative thereof.

Typical, non-limiting examples of Aminoglycoside antibacterial agents include amikacin, gentamicin, kanamycin, neomycin, netilmicin, tobramycin, paromomycin, arbekacin, streptomycin, apramycin and a like.

Typical, non-limiting examples of Ansamycin antibacterial agents include geldanamycin, herbimycin and a like.

Typical, non-limiting examples of Carbapenem antibacterial agents include ertapenem, doripenem, imipenem, meropenem, panipenem, biapenem, tebipenem, lenapenem, tomopenem and a like.

Typical, non-limiting examples of Lincosamide antibacterial agents include clindamycin, lincomycin and a like.

Typical, non-limiting examples of Macrolide antibacterial agents include azithromycin, clarithromycin, dirithromycin, erythromycin, roxithromycin, troleandomycin, telithromycin, spectinomycin, solithromycin and a like.

Typical, non-limiting examples of Monobactams antibacterial agents include aztreonam and a like.

Typical, non-limiting examples of Nitrofuran antibacterial agents include furazolidone, nitrofurantoin and a like.

Typical, non-limiting examples of Penicillin antibacterial agents include amoxicillin, ampicillin, azlocillin, carbenicillin, cloxacillin, dicloxacillin, flucloxacillin, mezlocillin, methicillin, nafcillin, oxacillin, penicillin g, penicillin v, piperacillin, temocillin, ticarcillin and a like.

Typical, non-limiting examples of Polypeptide antibacterial agents include bacitracin, colistin, polymyxin B and a like.

Typical, non-limiting examples of Quinolone antibacterial agents include ciprofloxacin, enoxacin, gatifloxacin, levofloxacin, lomefloxacin, moxifloxacin, nalidixic acid, levonadifloxacin, norfloxacin, ofloxacin, trovafloxacin, grepafloxacin, sparfloxacin, temafloxacin, fleroxacin, pefloxacin, sitafloxacin and a like.

Typical, non-limiting examples of Sulfonamide antibacterial agents include mafenide, sulfonamidochrysoidine, sulfacetamide, sulfadiazine, sulfamethizole, sulfamethoxazole, sulfasalazine, sulfisoxazole, trimethoprim and a like.

Typical, non-limiting examples of Tetracycline antibacterial agents include demeclocycline, doxycycline, minocycline, oxytetracycline, tetracycline, tigecycline and a like.

Typical, non-limiting examples of Oxazolidinone antibacterial agents include tedizolid, linezolid, ranbezolid, torezolid, radezolid and a like.

The pharmaceutical compositions according to the invention may include one or more pharmaceutically acceptable carriers or excipients or a like. Typical, non-limiting examples of such carriers or excipients include mannitol, lactose, starch, magnesium stearate, sodium saccharine, talcum, cellulose, sodium crosscarmellose, glucose, gelatine, sucrose, magnesium carbonate, wetting agents, emulsifying agents, solubilizing agents, pH buffering agents, lubricants, stabilizing agents, binding agents and a like.

The pharmaceutical compositions according to this invention can exist in various forms. In some embodiments, the pharmaceutical composition is in the form of a powder or a solution. In some other embodiments, the pharmaceutical compositions according to the invention are in the form of a powder that can be reconstituted by addition of a compatible reconstitution diluent prior to parenteral administration. Non-limiting example of such a compatible reconstitution diluent includes water.

In some other embodiments, the pharmaceutical compositions according to the invention are in the form of a frozen composition that can be diluted with a compatible diluent prior to parenteral administration.

In some other embodiments, the pharmaceutical compositions according to the invention are in the form ready to use for parenteral administration.

In the methods according to the invention, the pharmaceutical composition and/or other pharmaceutically active ingredients disclosed herein may be administered by any appropriate method, which serves to deliver the composition or its constituents or the active ingredients to the desired site. The method of administration can vary depending on various factors, such as for example, the components of the pharmaceutical composition and nature of the active ingredients, the site of the potential or actual infection, the microorganism (e.g. bacteria) involved, severity of infection, age and physical condition of the subject. Some non-limiting examples of administering the composition to a subject according to this invention include oral, intravenous, topical, intra-respiratory, intra-peritoneal, intra-muscular, parenteral, sublingual, transdermal, intranasal, aerosol, intraocular, intra-tracheal, intra-rectal, vaginal, gene gun, dermal patch, eye drop, ear drop or mouthwash.

The compositions according to the invention can be formulated into various dosage forms wherein the active ingredients and/or excipients may be present either together (e.g. as an admixture) or as separate components. When the various ingredients in the composition are formulated as a mixture, such composition can be delivered by administering such a mixture. The composition or dosage form wherein the ingredients do not come as a mixture, but come as separate components, such composition/dosage form may be administered in several ways. In one possible way, the ingredients may be mixed in the desired proportions and the mixture is then administered as required. Alternatively, the components or the ingredients (active or inert) may be separately administered (simultaneously or one after the other) in appropriate proportion so as to achieve the same or equivalent therapeutic level or effect as would have been achieved by administration of the equivalent mixture.

Similarly, in the methods according to the invention, the active ingredients disclosed herein may be administered to a subject in several ways depending on the requirements. In some embodiments, the active ingredients are admixed in appropriate amounts and then the admixture is administered to a subject. In some other embodiments, the active ingredients are administered separately. Since the invention contemplates that the active ingredients agents may be administered separately, the invention further provides for combining separate pharmaceutical compositions in kit form. The kit may comprise one or more separate pharmaceutical compositions, each comprising one or more active ingredients. Each of such separate compositions may be present in a separate container such as a bottle, vial, syringes, boxes, bags, and the like. Typically, the kit comprises directions for the administration of the separate components. The kit form is particularly advantageous when the separate components are preferably administered in different dosage forms (e.g., oral and parenteral) ore are administered at different dosage intervals. When the active ingredients are administered separately, they may be administered simultaneously or sequentially.

The pharmaceutical composition or the active ingredients according to the present invention may be formulated into a variety of dosage forms. Typical, non-limiting examples of dosage forms include solid, semi-solid, liquid and aerosol dosage forms; such as tablets, capsules, powders, solutions, suspensions, suppositories, aerosols, granules, emulsions, syrups, elixirs and a like.

In general, the compounds, pharmaceutical compositions and method disclosed herein are useful in treating and/or preventing bacterial infections. Advantageously, the compounds, compositions and methods disclosed herein are also effective in treating or preventing infections caused by bacteria that are considered be less or not susceptible to one or more of known antibacterial agents or their known compositions. Some non-limiting examples of such bacteria known to have developed resistance to various antibacterial agents include *Acinetobacter, E. coli, Pseudomonas aeruginosa, Staphylococcus aureus, Enterobacter, Klebsiella, Citrobacter* and a like. Other non-limiting examples of infections that may be treated or prevented using the compounds, compositions and/or methods according to the invention include: skin and soft tissue infections, febrile neutropenia, urinary tract infection, intraabdominal infections, respiratory tract infections, pneumonia (nosocomial), bacteremia meningitis, surgical infections etc.

Surprisingly, the compounds, compositions and methods according to the invention are also effective in treating and/or preventing bacterial infections that are caused by bacteria producing one or more beta-lactamase enzymes. The ability of the compounds, compositions and/or methods according to the present invention to treat such resistant bacteria with typical beta-lactam antibiotics represents a significant improvement in the art.

In general, the compounds of Formula (I) or a stereoisomer or pharmaceutically acceptable salt thereof according to invention are also useful in increasing antibacterial effectiveness of a antibacterial agent in a subject. The antibacterial effectiveness of one or more antibacterial agents may be increased, for example, by co-administering said antibacterial agent or a pharmaceutically acceptable derivative thereof with a compound of Formula (I) or a stereoisomer or a pharmaceutically acceptable salt thereof according to the invention.

In some embodiments, there is provided a process for preparation of a compound of Formula (Ia), Formula (Ia)

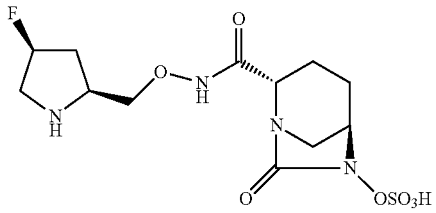

Comprising:

(a) converting a compound of Formula (IIa) into a compound of Formula (IIIa) in presence of a fluorinating agent;

(IIa)

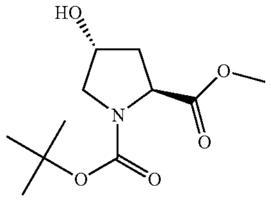

(IIIa)

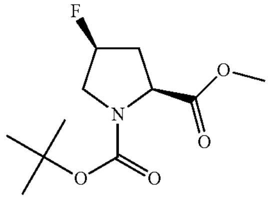

(b) converting a compound of Formula (IIIa) into a compound of Formula (IVa);

(IVa)

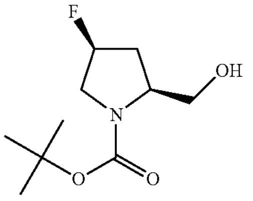

(c) converting a compound of Formula (IVa) into a compound of Formula (Va);

(Va)

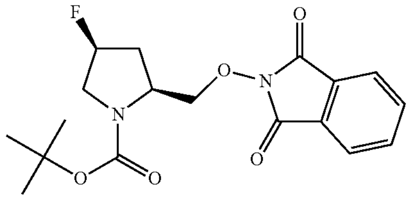

(d) converting a compound of Formula (Va) into a compound of Formula (VIa);

(VIa)

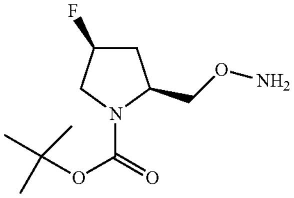

(e) reacting a compound of Formula (VIa) with a compound of Formula (VII) to obtain a compound of Formula (VIIIa);

(VII)

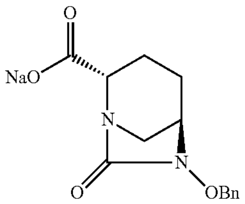

(VIIIa)

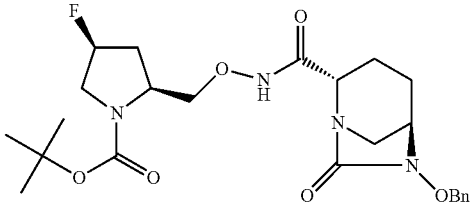

(f) converting a compound of Formula (VIIIa) into a compound of Formula (IXa);

(IXa)

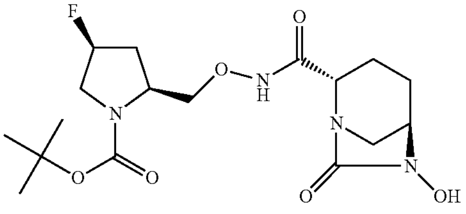

(g) converting a compound of Formula (IXa) into a compound of Formula (Xa); and (Xa)

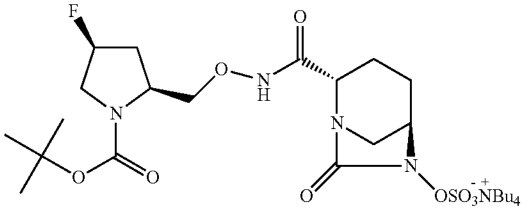

(h) converting a compound of Formula (Xa) into a compound of Formula (Ia).

In some embodiments, the compound of Formula (IIa) is converted into a compound of Formula (IIIa) in presence of a suitable fluorinating agent. Typical, non-limiting examples of suitable fluorinating agents include diethylaminosulfur trifluoride (DAST reagent).

In some other embodiments, the compound of Formula (IIIa) is converted into a compound of Formula (IVa) in presence of a suitable reducing agent. Typical, non-limiting examples of suitable reducing agents include lithium borohydride.

In some other embodiments, the compound of Formula (IVa) is converted into a compound of Formula (Va) in presence of suitable reagents. Typical, non-limiting examples of these reagents include diisopropylazodicarboxylate, triphenylphosphine, and N-hydroxy phthalimide.

In some embodiments, the compound of Formula (Va) is converted into a compound of Formula (VIa) using suitable reagents. Typical, non-limiting examples of these reagents include hydrazine hydrate.

In some other embodiments, the compound of Formula (VIIIa) is obtained by reacting a compound of Formula (VIa) with sodium salt of (2S, 5R)-6-benzyloxy-7-oxo-1,6-diazabicyclo [3.2.1]octane-2-carboxylic acid (VII) in presence of suitable reagents. Typical, non-limiting examples of these reagents include 1-hydroxybenzotriazole (HOBt), 1-ethyl-3-(3-dimethylaminopropyl)carbodiimide hydrochloride (EDC.HCl) and N-Methyl Morpholine (NMM).

In some embodiments, the compound of Formula (VIIIa) is converted into a compound of Formula (IXa) in presence of a suitable debenzylating agent. Typical, not-limiting examples of suitable debenzylating agents include hydrogen gas in presence of a transition metal catalyst such as palladium on carbon.

In some embodiments, the compound of Formula (IXa) is converted into a compound of Formula (Xa) in presence of a suitable sulfonating agent followed by a treatment with tetrabutylammonium acetate. Typical, not-limiting examples of suitable sulfonating agents include sulfur trioxide dimethylformamide complex. The sulfonation reaction is followed by treatment with tetrabutylammonium acetate to obtain a compound of Formula (Xa).

In some embodiments, the compound of Formula (Xa) is converted into a compound of Formula (Ia) in presence of a suitable deprotecting agent. Typical, not-limiting examples of suitable deprotecting agents include trifluoroacetic acid.

A wide variety of other reagents which can bring about these functional transformations can be used. It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

(2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide (Ia)

(Ia)

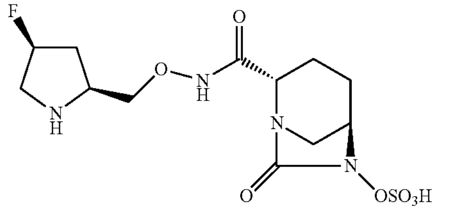

Step 1: Synthesis of 1-tert-butyl-2-methyl (2S, 4S)-4-fluoropyrrolidine-1,2-dicarboxylate (IIIa).

A stirred solution of 1-tert-butyl-2-methyl (2S, 4R)-4-hydroxy pyrrolidine-1,2-dicarboxylate (IIa) (10 g, 40.8 mmol) in dichloroethane (100 ml) was cooled to −78° C. and diethylaminosulfur trifluoride (8.2 ml, 61.2 mmol) was added to the solution. The reaction contents were stirred at this temperature for 2 hours and later quenched by adding saturated aqueous solution of $NaHCO_3$ (10 ml). The organic layer was separated, washed with brine and dried over sodium sulfate. The dried organic layer was concentrated under reduced pressure to obtain the compound (IIIa) as thick oil (7 g, yield: 69%).

Analysis:

Mass: 248.2 (M+H);

$^1$H NMR (400 MHz, $CDCl_3$): δ 5.20 (dm, $^2J_{H-F}$=53.2 Hz, 1H), 4.55-4.42 (m, 1H), 3.89-3.79 (m, 1H), 3.75 (s, 3H), 3.70-3.61 (m, 1H), 2.53-2.31 (m, 2H), 1.48 and 1.43 (2 s, 9H).

Step 2: Synthesis of tert-butyl (2S, 4S)-4-fluoro-2-(hydroxymethyl)pyrrolidine-1-carboxylate (IVa).

To a stirred solution of compound (IIIa) (7 g, 28.3 mmol) in Tetrahydrofuran (70 ml) and Methanol (70 ml) was added anhydrous Lithium Chloride (2.61 g, 62.3 mmol) followed by sodium borohydride (2.69 g, 70.8 mmol) at a room temperature. The reaction contents were stirred for 6 hours at this temperature, and then concentrated under reduced pressure. The residue so obtained was partitioned between ethyl acetate (100 ml) and water (100 ml). The organic layer was separated, dried over sodium sulfate and concentrated under reduced pressure to obtain a crude product, which was purified by column chromatography (silica gel 60-120 mesh size; eluent: mixture of acetone: hexane 30:70 v/v). The combined fractions were concentrated to obtain the compound (IVa) as oil (6 g, yield: 97%).

Analysis:

Mass: 220.3 (M+H);

$^1$H NMR (400 MHz, $CDCl_3$): δ 5.22 (dm, J=52.8 Hz, 1H), 4.17-4.09 (m, 2 H), 3.87-3.82 (m, 1 H), 3.74-3.49 (m, 3H), 2.35-2.19 (m, 1H), 2.05-1.97 (m, 1H), 1.48 (s, 9H).

Step 3: Synthesis of tert-butyl (2S, 4S)-2-{[(1,3-dioxo-1,3-dihydro-2H-isoindol-2-yl)oxy]methyl}-4-fluoropyrrolidine-1-carboxylate (Va).

Diisopropylazodicarboxylate (8.3 g, 41 mmol) was added to a solution of compound (IVa) (6 g, 27 mmol) in tetrahydrofuran (100 ml) followed by addition of triphenylphosphine (10.76 g, 41 mmol) and N-hydroxy phthalimide (4.46 g, 27 mmol) under stirring at room temperature (exothermic reaction, temperature controlled by water cooling). The stirring was continued for 16 hours at room temperature after the addition was complete. The reaction progress was monitored using Thin Layer Chromatography (TLC). The reactions contents were then concentrated under reduced pressure to obtain a crude product, which was purified by column chromatography (silica gel 60-120 mesh size; eluent: mixture of acetone: hexane 30:70 v/v). The combined fractions were concentrated to obtain compound (Va) as a white solid (9 g, yield: 90%).

Analysis:

Mass: 365.3 (M+H);

$^1$H NMR (400 MHz, $CDCl_3$): δ 7.83-7.75 (m, 4H), 5.27 (dm, $^2J_{H-F}$=51.2 Hz, 1H), 5.01-4.95 (m, 1H), 4.51-4.46 (m, 1H), 4.32-4.20 (m, 2H), 3.75-3.45 (m, 2H), 2.82-2.74 (m, 1H), 2.32-2.17 (m, 1H), 1.42 and 1.39 (2 s, 9H).

Step 4: Synthesis of tert-butyl (2S, 4S)-2-[(aminooxy)methyl]-4-fluoropyrrolidine-1-carboxylate (VIa).

Hydrazine hydrate (2.4 g, 48 mmol) was added to a solution of compound (Va) (9 g, 24 mmol) in dichloromethane (100 ml) under stirring, at room temperature. Stirring was continued further for 2 hours at room temperature, and the reaction progress was monitored using TLC. The reaction mixture was filtered through a celite bed under suction and the residue was washed with fresh dichloromethane (20 ml). The combined filtrate washed with 10% aqueous $NaHCO_3$ solution (2×50 ml) followed by brine (50 ml). The resulting solution was dried over sodium sulfate and then concentrated under reduced pressure to obtain the compound (VIa) as oil (5.7 g, yield: ~100%).

Step 5: Synthesis of (2S, 5R)-N-{[1-tert-butoxycarbonyl (2S, 4S)-4-fluoropyrrolidin-2-yl]methoxy}-6-benzyloxy-7-oxo-1,6-diazabicyclo[3.2.1]octane-2-carboxamide (VIIIa).

N-(3-dimethylaminopropyl)-N'-ethylcarbodiimide hydrochloride (EDC.HCl, 7.87 g, 41.2 mmol), N-methylmorpholine (NMM, 8.32 g, 82.4 mmol) and 1-Hydrxybenzotriazole (HOBT, 3.7 g, 27.4 mmol) were added successively to a stirred solution of sodium salt of (2S, 5R)-6-benzyloxy-7-oxo-1,6-diazabicyclo [3.2.1] octane-2-carboxylic acid (VII) (8.21 g, 27.4 mmol) in DMF (100 ml) at room temperature. Compound (VII) was prepared using the procedure disclosed in International Patent Application No PCT/IB2013/059264. To this solution was further added a solution of compound (VIa) (5.7 g, 24.3 mmol) in DMF (15 ml) and the stirring was continued further for 16 hours. The reaction mixture was poured into water (500 ml), stirred well and extracted with ethyl acetate (2×200 ml). The organic layer was dried over sodium sulfate and then concentrated under reduced pressure to obtain an oily residue, which was purified using column chromatography (silica gel 60-120 mesh size; eluent: mixture of acetone: hexane 40:60 v/v). The combined fractions were evaporated to obtain compound (VIIIa) as a white solid (9.0 g, yield: 75%).

Analysis:

Mass: 493.3 (M+H);

$^1$H NMR (400 MHz, $CDCl_3$): δ 10.14 (bs, 1H), 7.36-7.26 (m, 5H), 5.23 (dm, 1H, J=59.6 Hz), 5.05 (d, 1H, J=11.2 Hz), 4.90 (d, 1H, J=11.2 Hz), 4.29-4.28 (m, 1H), 3.94-3.83 (m, 3H), 3.72-3.56 (m, 2H), 3.32-3.3.29 (m, 1H), 3.07-2.89 (m, 2H), 2.29-1.82 (m, 6H), 1.46 (s, 9H)

Step-6: Synthesis of (2S, 5R)-N-{[1-tert-butoxycarbonyl (2S, 4S)-4-fluoropyrrolidin-2-yl]methoxy}-6-hydroxy-7-oxo-1,6-diazabicyclo[3.2.1]octane-2-carboxamide (IXa).

The compound (VIIIa) (5 g, 10.1 mmol) was hydrogenated by purging hydrogen gas in presence of 10% palladium on carbon (2 g, 50% wet) as a catalyst and 1:1 mixture of dichloromethane (25 ml) and dimethylformamide (25 ml) as a solvent, at a temperature of 25-30° C. The progress of reaction was monitored with the help of a TLC (ethyl acetate: hexane, 1:1). After completion of the reaction, the reaction contents were filtered through celite bed. The filtrate was concentrated under reduced pressure to obtain a crude compound (IXa) (4 g, yield: ~100%).

Step-7: Synthesis of tetrabutylammonium salt of (2S, 5R)-N-{[1-tert-butoxycarbonyl (2S, 4S)-4-fluoropyrrolidin-2-yl] methoxy}-7-oxo-6-(sulfooxy)-1,6-diazabicyclo[3.2.1]octane-2-carboxamide (Xa).

Dimethylformamide sulphurtrioxide complex (3.1 g, 20.2 mmol) was added to a stirred solution of compound (IXa) (4.0 g, 10.1 mmol) in DMF (30 ml) under argon atmosphere at 25° C. The stirring was continued for 1 hour at 25° C., and the reaction was monitored using a TLC. A solution of tetrabutylammonium acetate (7.64 g, 25 mmol) in water (15 ml) was added to the reaction mixture and stirring continued further for 1 hour and the resulting mixture was concentrated under reduced pressure at 40° C. The residue was diluted with water (50 ml) and the mixture was extracted in (2×50 ml) dichloromethane. The combined organic layer was dried over $Na_2SO_4$ and evaporated under reduced pressure to obtain an oil, which was purified by column chromatography (silica gel 60-120 mesh size; eluent: mixture of dichloromethane: methanol, 95:5 v/v) and evaporation of the combined fractions under reduced pressure gave the compound (Xa) as white foam (4g, yield: 54%).

Analysis:

Mass: 481.4(M-H).

$^1H$ NMR (400 MHz, $CDCl_3$): δ 10.22 (bs, 1H), 5.23 (dm, 1H, J=54 Hz), 4.34-4.35 (m, 2H), 3.91-4.14 (m, 4H), 3.59-3.73 (m, 2H), 3.25-3.36 (m, 9H), 2.95 (d, 1H, J=9.2Hz), 2.08-2.34 (m, 4H), 1.89-1.91 (m, 1H), 1.63-1.77 (m,12H), 1.40-1.53 (m, 16H), 0.98-1.02 (t, 12H).

Step-8: Synthesis of (2S, 5R)-N-{[(2S, 4S)-4-fluoropyrrolidin-2-yl]methyloxy}-7-oxo-6-(sulfooxy)-1,6-diazabicyclo [3.2.1]octane-2-carboxamide (Ia).

Compound (Xa) (4 g, 5.52 mmol) was dissolved in dichloromethane (20 ml) and the solution was cooled to −15° C. Trifluoroacetic acid (20 ml) was added drop-wise to the solution at −10° to −15° C. The reaction was monitored by ES-MS analysis. The temperature of the solution was maintained at −10 to −5° C. for 1 hour. After completion of the reaction, hexane (200 ml) was added to the reaction mixture. The hexane layer was decanted and the oily residue was washed thoroughly by hexane (2×100 ml) and diethyl ether (50 ml). The solid residue formed was further washed with acetonitrile and diethyl ether (20 ml each). The residue was dried under reduced pressure to obtain the product as a white solid, which was recrystallized using a mixture of isopropanol and water to obtain the compound of formula (Ia) as a white solid (1.7 g, yield: 80%).

Analysis:

Mass: 381.2 (M-H); for Molecular weight: 382.2; Molecular Formula: $C_{12}FH_{19}N_4O_7S$.

$^1H$ NMR (400 MHz, DMSO-$d_6$): δ 11.67 (bs, 1H), 9.22 (bs, 1H), 5.43 (dm, $^2J_{H\text{-}F}$=53.2 Hz, 1H), 4.05-3.95 (m, 4H), 3.81 (d, J=6 Hz, 1H), 3.62-3.32 (m, 4H), 3.06-2.95 (m, 2H), 2.07-1.67 (m, 5H).

Melting Point: 180-183° C. (Decomposition).

Example 2

(2S, 5R)-N-{[(2S, 4R)-4-fluoropyrrolidin-2-yl] methyloxy}-7-oxo-6-(sulfooxy)-1,6-diazabicyclo [3.2.1]octane-2-carboxamide (Ib)

(Ib)

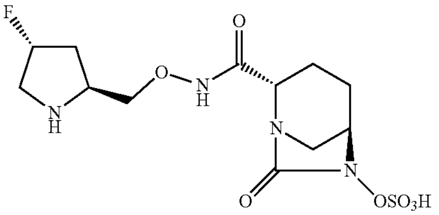

Compound of Formula (Ib) was prepared according to the procedure described in Example 1, starting with 1-tert-butyl-2-methyl (2S, 4S)-4-hydroxy pyrrolidine-1,2-dicarboxylate (compound (IIb)), in about 24% overall yield.

(IIb)

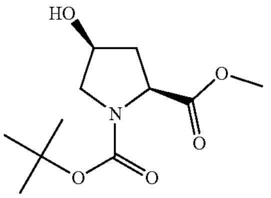

Analysis:

Mass: 381.2 (M-H); for Molecular weight: 382.2; Molecular Formula: $C_{12}FH_{19}N_4O_7S$.

$^1H$ NMR (400MHz, DMSO-$d_6$): δ 11.72 (brs, 1 H), 9.37 (brs, 1 H), 5.45 (d, $^2J_{H\text{-}F}$=52.8 Hz, 1 H), 4.11-3.92 (m, 4 H), 3.82 (d, J=4.4 Hz, 1 H), 3.62-3.43 (m, 3 H), 3.05-2.96 (m, 2 H), 2.42-2.32 (m, 1 H), 2.15-1.82 (m, 3 H), 1.75-1.63 (m, 2 H).

Melting Point: 160-163° C. (Decomposition).

Example 3

(2S, 5R)-N-{[(2R, 4S)-4-fluoropyrrolidin-2-yl] methyloxy}-7-oxo-6-(sulfooxy)-1,6-diazabicyclo [3.2.1]octane-2-carboxamide (Ic)

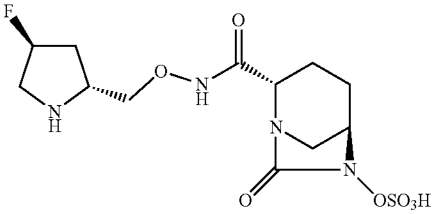

Compound of Formula (Ic) was prepared according to the procedure described in Example 1, starting with 1-tert-butyl-2-methyl (2R, 4R)-4-hydroxy pyrrolidine-1,2-dicarboxylate (compound (IIc)), in about 16% overall yield.

(IIc)

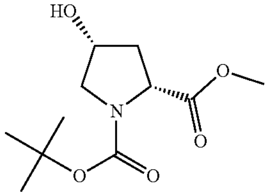

Analysis:

Mass: 381.2 (M-H); for Molecular weight: 382.2; Molecular Formula: $C_{12}FH_{19}N_4O_7S$.

$^1$H NMR (400MHz, DMSO-$d_6$): δ 11.74 (bs, 1H), 9.21 (bs, 1H), 5.42 (dm, $^2J_{H\text{-}F}$=52.4 Hz, 1H), 4.11-3.95 (m, 4H), 3.79-3.73 (m, 2H), 3.53-3.42 (m, 4H), 3.11-2.95 (m, 1H), 2.01-1.62 (m, 5H).

Melting Point: 175-178° C. (Decomposition).

Example 4

(2S, 5R)-N-{[(2R, 4R)-4-fluoropyrrolidin-2-yl] methyloxy}-7-oxo-6-(sulfooxy)-1,6-diazabicyclo [3.2.1]octane-2-carboxamide (Id)

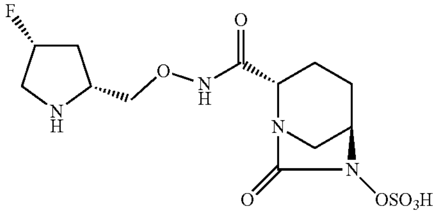

Compound of Formula (Id) was prepared according to the procedure described in Example 1, starting with 1-tert-butyl-2-methyl (2R, 4S)-4-hydroxy pyrrolidine-1,2-dicarboxylate (compound (IId)), in about 16% overall yield.

(IId)

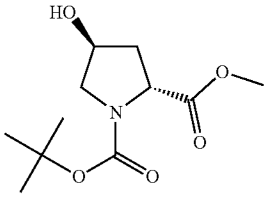

Analysis

Mass: 381.2 (M-H); for Molecular weight: 382.2; Molecular Formula: $C_{12}FH_{19}N_4O_7S$.

$^1$H NMR (400MHz, DMSO-$d_6$): ≢7 11.27 (bs, 1H), 9.18 (bs, 1H), 5.42 (dm, $^2J_{H\text{-}F}$=53.2 Hz, 1H), 4.02-3.92 (m, 4H), 3.80 (d, J=6Hz, 1H), 3.59-3.31 (m, 4H), 3.05-2.98 (m, 1H), 2.45-2.38 (m, 1H), 2.03-1.65 (m, 5H).

Melting Point: 207-209° C. (Decomposition).

BIOLOGICAL ACTIVITY

The biological activity of representative compounds according to the invention against various bacterial strains was investigated. In a typical study, overnight grown bacterial cultures were diluted appropriately and inoculated on the agar media containing doubling dilutions of the test compounds. Observation for growth or no growth was performed after 16-20 hours of incubation at 35±2° C. in ambient air. The overall procedure was performed as per Clinical and Laboratory Standards Institute (CLSI) recommendations (Clinical and Laboratory Standards Institute (CLSI), Performance Standards for Antimicrobial Susceptibility Testing, 20th Informational Supplement, M 100-S20, Volume 30, No. 1, 2010). The results of these studies are summarized in Table 1.

TABLE 1

Antibacterial activity of compounds according to the invention (MIC expressed in μg/ml)

| Sr. Bacterial strain | MIC (expressed in μg/ml) of a compound according to | | | |
|---|---|---|---|---|
| | Example 1 | Example 2 | Example 3 | Example 4 |
| 1. *K. pneumoniae* ATCC 700603 | >32 | >32 | >32 | >32 |
| 2. *E. coli* 13351 | 0.5 | 1 | 1 | 2 |
| 3. *E. coli* 13352 | 1 | 2 | 2 | 4 |
| 4. *E. coli* 13353 | 0.5 | 1 | 1 | 1 |
| 5. *E. coli* M 36 | 0.25 | 1 | 1 | 1 |
| 6. *E. coli* 7MP | 1 | 2 | 2 | 4 |
| 7. *E. coli* M 49 | 4 | 4 | 4 | 4 |
| 8. *E. coli* M 50 | 0.5 | 2 | 1 | 2 |
| 9. *E. coli* M 138 | 0.5 | 2 | 1 | 2 |
| 10. *K. pneumoniae* H521 | 1 | 4 | 2 | 4 |
| 11. *K. pneumoniae* H522 | 1 | 4 | 2 | 4 |
| 12. *K. pneumoniae* H523 | 1 | 4 | 2 | 4 |
| 13. *K. pneumoniae* H525 | 0.5 | 4 | 2 | 2 |

As can be seen, the compound according to the invention exhibit antibacterial activity against various bacterial strains, including those which are known to be resistant to one or more of the existing antibacterial agents. The antibacterial activity of compounds according to the invention was also investigated in combination with several antibacterial agents, including Cefepime, Ceftazidime, Cefixime, Cefpodoxime, and Ceftibuten. For example, antibacterial activity of the compound according to Example 1 in combination with various antibacterial agents is summarized in Table 2.

In these studies, the initial bacterial count (at 0 hours) was 7.18 $\log_{10}$ CFU/ml. In general, 1, 2 and 3 log bacterial kill over initial count corresponds to 99%, 99.9% and 99.99% bactericidal effect. In a typical time-dependent bacterial kill studies, freshly grown bacterial cultures were diluted to target cell density (initial starting inoculum) in Cation adjusted Muller Hinton broth medium (BD, USA). The antibacterial agents (either alone or in combination) at the required concentrations were added into the culture-containing medium. The sample flasks were incubated under shaking condition (120 rpm) at 37° C. Enumeration of viable bacterial count was undertaken periodically by diluting the sample in normal saline and plating on to the Tryptic Soya Agar plates (BD, USA). The plates were incubated for 24 hours to estimate viable bacterial count. The results are expressed in terms of $\mathrm{Log}_{10}$ CFU per ml.

Several compositions containing the compounds according to the invention, alone and in combination with antibacterial agents were also prepared.

TABLE 2

Time dependant % bacterial kill effect for a combination of a compound according to Example 1 with various antibacterial agents, against *E. coli* strain M50 (CMY, DHA)

| | | Bacterial count ($Log_{10}$ CFU per ml) | | | |
|---|---|---|---|---|---|
| Sr. | Active ingredient | 2 hours | 4 hours | 6 hours | 8 hours |
| 1. | Control (No active ingredient) | 8.04 | 8.40 | 8.74 | 9.08 |
| 2. | Cefepime (8 μg/ml) | 7.85 | 8.65 | 8.90 | 9.0 |
| 3. | Ceftazidime (8 μg/ml) | 7.81 | 8.90 | 9.0 | 8.92 |
| 4. | Cefixime (8 μg/ml) | 7.85 | 8.90 | 8.78 | 9.04 |
| 5. | Cefpodoxime (8 μg/ml) | 7.95 | 8.70 | 8.95 | 9.30 |
| 6. | Ceftibuten (8 μg/ml) | 7.98 | 8.30 | 8.74 | 9.48 |
| 7. | Compound of Formula (Ia) (4 μg/ml) | 7.78 | 6.74 | 5.85 | 6.13 |
| 8. | Cefepime (1 μg/ml) + Compound of Formula (Ia) (4 μg/ml) | 4.30 | 3.48 | 3.0 | 2.86 |
| 9. | Ceftazidime (2 μg/ml) + Compound of Formula (Ia) (4 μg/ml) | 3.85 | 3.48 | 3.0 | 1.6 |
| 10. | Cefixime (1 μg/ml) + Compound of Formula (Ia) (4 μg/ml) | 7.18 | 4.74 | 4.08 | 4.6 |
| 11. | Cefpodoxime (2 μg/ml) + Compound of Formula (Ia) (4 μg/ml) | 5.02 | 4.28 | 3.0 | 3.0 |
| 12. | Ceftibuten (8 μg/ml) + Compound of Formula (Ia) (4 μg/ml) | 7.0 | 5.70 | 4.30 | 4.0 |

The invention claimed is:

1. A compound of Formula (I),

Formula (I)

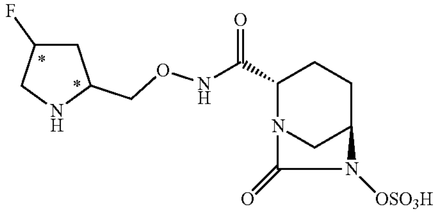

or a stereoisomer or a pharmaceutically acceptable salt thereof.

2. The compound according to claim 1, selected from:

(2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide; and stereoisomer and pharmaceutically acceptable salts thereof.

3. The compound according to claim 1, selected from:

Sodium salt of (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide; and stereoisomers thereof.

4. A pharmaceutical composition comprising a compound according to claim 1.

5. The pharmaceutical composition according to claim 4, further comprising at least one antibacterial agent or pharmaceutically acceptable salt thereof.

6. The pharmaceutical composition according to claim 5, wherein each of the at least one antibacterial agent is a beta-lactam antibacterial agent.

7. The pharmaceutical composition according to claim 5, wherein each of the at least one antibacterial agent is independently selected from ansamycin, carbacephem, carbapenam, carbapenem, cephalosporin, cephamycin, cephem, lincosamide, lipopeptide, macrolide, ketolide, monobactam, nitrofuran, oxacephem, oxapenam, oxazolidinone, penam, penem, penicillin, polypeptide, quinolone, sulfonamide, and tetracycline antibacterial agents.

8. The pharmaceutical composition according to claim 5, wherein each of the at least one antibacterial agent is independently selected from cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefclidin, cefdaloxime, cefdinir, cefditoren, cefepime, cefetamet, cefixime, cefluprenam, cefmenoxime, cefmetazole, cefminox, cefodizime, cefonicid, cefoperazone, ceforanide, cefoselis, cefotaxime, cefotetan, cefotiam, cefovecin, cefoxitin, cefoxitin, cefozopran, cefpimizole, cefpiramide, cefpirome, cefpodoxime, cefprozil, cefquinome, cefradine, cefroxadine, cefsulodin, ceftaroline, ceftazidime, cefteram, ceftezole, ceftibuten, ceftiofur, ceftiolene, ceftizoxime, ceftobiprole, ceftolozane, ceftriaxone, cefuroxime, cefuzonam, cephaloridine, cephradine, flomoxef, latamoxef, loracarbef, moxalactam, and pharmaceutically acceptable salts thereof.

9. The pharmaceutical composition according to claim 5, wherein each of the at least one antibacterial agent is independently selected from cefaclor, cefadroxil, cefalexin, cefdinir, cefixime, cefpirome, cefpodoxime, cefprozil, cefradine, ceftibuten, cefuroxime, loracarbef, and pharmaceutically acceptable salts thereof.

10. A method for treating bacterial infection in a subject, said method comprising administering to said subject a compound as in one of claims 1-3.

11. A method for treating bacterial infection in a subject, said method comprising administering to said subject a pharmaceutical composition as in one of the claims 4-9.

12. A method for treating bacterial infection in a subject, said method comprising administering to said subject: (a) a compound of Formula (I) according to claim 1 or a stereoisomer or a pharmaceutically acceptable salt thereof, and (b) at least one antibacterial agent or pharmaceutically acceptable salt thereof.

13. The method according to claim 12, wherein the compound of Formula (I) is:

(2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

(2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

or a stereoisomer or a pharmaceutically acceptable salt thereof.

14. The method according to claim 12, wherein the compound of Formula (I) is:

Sodium salt of (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

Sodium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

Potassium salt of (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide;

Potasium salt of (2S, 5R)-N-{[(2S, 4R)-4-fluoropyrrolidin-2-yl]methyloxy}-7-oxo-6-(sulfooxy)-1,6-diazabicyclo[3.2.1]octane-2-carboxamide;

Potasium salt of (2S, 5R)-N-{[(2R, 4S)-4-fluoropyrrolidin-2-yl]methyloxy}-7-oxo-6-(sulfooxy)-1,6-diazabicyclo[3.2.1]octane-2-carboxamide;

Potasium salt of (2S, 5R)-N-{[(2R, 4R)-4-fluoropyrrolidin-2-yl]methyloxy}-7-oxo-6-(sulfooxy)-1,6-diazabicyclo[3.2.1]octane-2-carboxamide;

or a stereoisomer thereof.

15. The method according to claim 12, wherein each of the at least one antibacterial agent is a beta-lactam antibacterial agent.

16. The method according to claim 12, wherein each of the at least one antibacterial agent is independently selected from ansamycin, carbacephem, carbapenam, carbapenem, cephalosporin, cephamycin, cephem, lincosamide, lipopeptide, macrolide, ketolide, monobactam, nitrofuran, oxacephem, oxapenam, oxazolidinone, penam, penem, penicillin, polypeptide, quinolone, sulfonamide, and tetracycline antibacterial agents.

17. The method according to claim 12, wherein each of the at least one antibacterial agent is independently selected from cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefclidin, cefdaloxime, cefdinir, cefditoren, cefepime, cefetamet, cefixime, cefluprenam, cefmenoxime, cefmetazole, cefminox, cefodizime, cefonicid, cefoperazone, ceforanide, cefoselis, cefotaxime, cefotetan, cefotiam, cefovecin, cefoxitin, cefoxitin, cefozopran, cefpimizole, cefpiramide, cefpirome, cefpodoxime, cefprozil, cefquinome, cefradine, cefroxadine, cefsulodin, ceftaroline, ceftazidime, cefteram, ceftezole, ceftibuten, ceftiofur, ceftiolene, ceftizoxime, ceftobiprole, ceftolozane, ceftriaxone, cefuroxime, cefuzonam, cephaloridine, cephradine, flomoxef, latamoxef, loracarbef, moxalactam, and pharmaceutically acceptable salts thereof.

18. The method according to claim 12, wherein each of the at least one antibacterial agent is independently selected from cefaclor, cefadroxil, cefalexin, cefdinir, cefixime, cefpirome, cefpodoxime, cefprozil, cefradine, ceftibuten, cefuroxime, loracarbef, and pharmaceutically acceptable salts thereof.

19. A compound which is (2S, 5R)-N-{[(2S, 4S)-4-fluoropyrrolidin-2-yl]methyloxy}-7-oxo-6-(sulfooxy)-1,6-diazabicyclo[3.2.1]octane-2-carboxamide, or a stereoisomer or a pharmaceutically acceptable salt thereof.

20. A pharmaceutical composition comprising a compound according to claim 19.

21. The pharmaceutical composition according to claim 20, further comprising at least one antibacterial agent or pharmaceutically acceptable derivative thereof.

22. The pharmaceutical composition according to claim 21, wherein each of the at least one antibacterial agent is a beta-lactam antibacterial agent.

23. The pharmaceutical composition according to claim 21, wherein each of the at least one antibacterial agent is independently cefixime, cefpodoxime, ceftibuten, cefuroxime, or a pharmaceutically acceptable salt thereof.

24. A method for treating bacterial infection in a subject, said method comprising administering to said subject a compound according to claim 19.

25. A method for treating bacterial infection in a subject, said method comprising administering to said subject a pharmaceutical composition as in one of claims 20-23.

26. A process for preparation of a compound of Formula (Ia):

Formula (Ia)

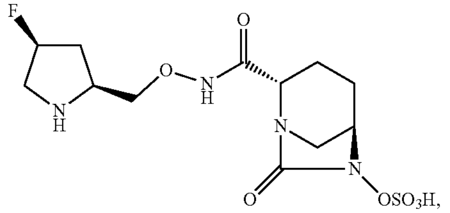

comprising:

(a) converting a compound of Formula (IIa) into a compound of Formula (IIIa) in the presence of a fluorinating agent:

(IIa)

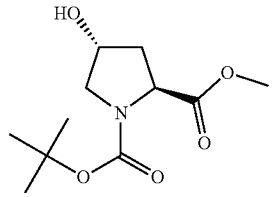

-continued (IIIa)

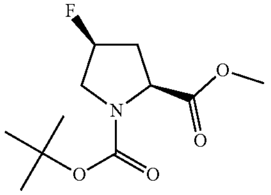

(b) converting a compound of Formula (IIIa) into a compound of Formula (IVa):

(IVa)

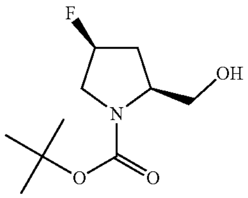

(c) converting a compound of Formula (IVa) into a compound of Formula (Va):

(Va)

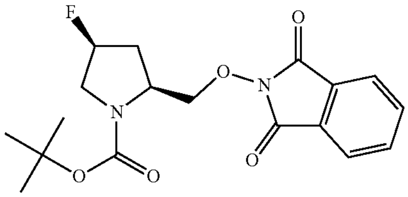

(d) converting a compound of Formula (Va) into a compound of Formula (VIa):

(VIa)

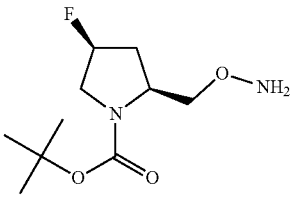

(e) reacting a compound of Formula (VIa) with a compound of Formula (VII) to obtain a compound of Formula (VIIIa):

(VII)

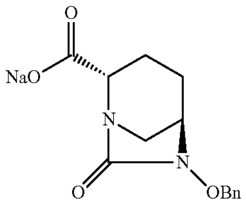

(VIIIa)

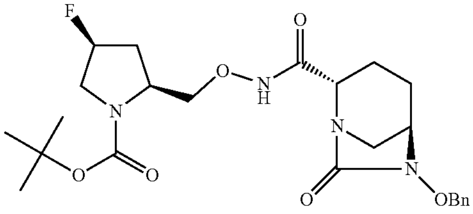

(f) converting a compound of Formula (VIIIa) into a compound of Formula (IXa):

(IXa)

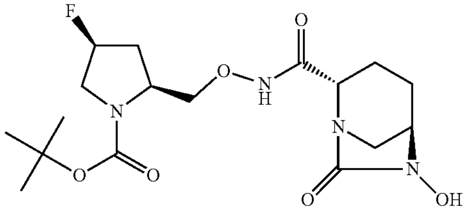

(g) converting a compound of Formula (IXa) into a compound of Formula (Xa):

(Xa)

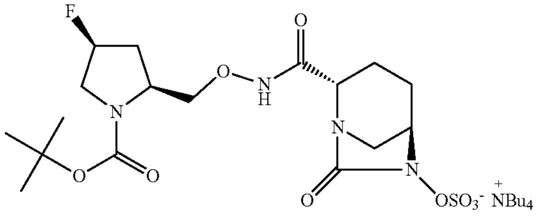

and (h) converting a compound of Formula (Xa) into the compound of Formula (Ia).

* * * * *